United States Patent [19]

Osterholt et al.

[11] Patent Number: 6,121,466

[45] Date of Patent: Sep. 19, 2000

[54] PROCESS FOR THE PREPARATION OF MACROCYCLIC ESTERS

[75] Inventors: Clemens Osterholt, Dorsten; Josef Metz; Günther Köhler, both of Marl; Marcel Feld, Köln, all of Germany

[73] Assignee: Huels Aktiengesellschaft, Marl, Germany

[21] Appl. No.: 09/261,227

[22] Filed: Mar. 3, 1999

[30] Foreign Application Priority Data

Mar. 3, 1998 [DE] Germany .................... 198 08 843

[51] Int. Cl.$^7$ .................................................. C07D 321/00
[52] U.S. Cl. ................................................. 549/267
[58] Field of Search ..................................... 549/347, 267

[56] References Cited

U.S. PATENT DOCUMENTS 5,717,111 2/1998 Koehler et al. ...................... 549/266

Primary Examiner—Amelia Owens
Attorney, Agent, or Firm—Oblon, Spivak, McClelland, Maier & Neustadt, P.C.

[57] ABSTRACT

The invention relates to a process for the preparation of a macrocyclic ester of the general formula:

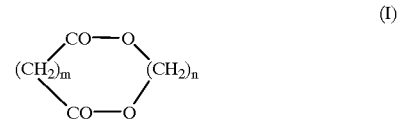

(I)

in which m is an integer from 6 to 14 and n is an integer from 2 to 12.

20 Claims, No Drawings

PROCESS FOR THE PREPARATION OF MACROCYCLIC ESTERS

BACKGROUND OF THE INVENTION

1. Field of the Invention

The invention relates to a process for the preparation of macrocyclic, preferably from 12- to 20-membered, esters of the general formula (I):

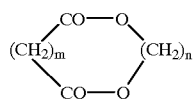
(I)

in which m is an integer from 6 to 14 and n is an integer from 2 to 12, from dicarboxylic acid glycol esters of the general formulae:

formula (II) HO—$(CH_2)_n$—O—CO—$(CH_2)_m$—CO—O—$(CH_2)_n$—OH;

formula (III) H{O—$(CH_2)_n$—O—CO—$(CH_2)_m$—CO}$_x$—O—$(CH_2)$n—OH;

formula (IV) H{O—$(CH_2)_n$—O—CO—$(CH_2)_m$—CO—}$_x$—OH; and/or formula (V) HO—CO—$(CH_2)_m$—CO—{—O—$(CH_2)_n$—O—CO—$(CH_2)_m$—CO—}$_x$—OH, in which m and n are as defined above and x is an integer >1, preferably from 2 to 10.

Cyclic esters of this type and in particular the cyclic ethylene brassylate, formed from the monomeric units brassylic acid and ethylene glycol, are extremely important in the perfume industry as a constituent of perfumes having an ambergris or musk note or as a fixative in fragrance mixtures.

2. Discussion of the Related Art

It is known to obtain macrocyclic esters by cyclizing depolymerization of oligomeric or polymeric glycol esters of corresponding carboxylic acids. The depolymerization is normally carried out at high temperatures and under reduced pressure in such a way that the resulting target products can be distilled off and obtained by condensation. The cyclizing depolymerization is described, for example, in *J. Am. Chem. Soc.* 57 (1935), 929–34 and U.S. Pat. No. 4,175,321.

It is further disclosed in U.S. Pat. No. 4,709,058, JA-B 55-120 581 and DE 32 25 341, that the preparation of macrocyclic esters by cyclizing depolymerization is advantageously carried out using inert high-boiling reaction media. A significant problem with any cyclizing depolymerization is that, under the reaction conditions, it is also possible for relatively high molecular weight esters to form through polycondensation of oligomers or polymers having terminal carboxyl groups with other oligomers or polymers which carry terminal hydroxyl groups, with the elimination of water, or through polycondensation of oligomers or polymers having terminal hydroxyalkyl groups with the elimination of glycol. The desired intramolecular formation of the macrocyclic monomeric target products is thus accompanied by an undesired intermolecular formation of linear, unreactive highly polymeric esters. However, this not only reduces the yield of the intended product, but also causes considerable process engineering problems.

SUMMARY OF THE INVENTION

In the processes, in accordance with the present invention, the reaction is generally carried out batchwise or semi-continuously. For a synthesis on a small scale, for example on a laboratory or pilot-plant scale, this presents no problem. Transferring the process to an industrial scale, however, causes problems, and, in particular, carrying out a reaction batchwise or continuously in a stirred reactor has considerable disadvantages. This is because the relatively high molecular weight products formed lower the thermal conductivity of the reaction mixture, while at the same time the viscosity increases. This hinders removal of the monomeric target products by distillation, which in turn favors the formation of relatively high molecular weight products. The amount of high molecular weight products thus increases, which results in an increasing amount of bottom product being formed, which must be disposed of. If the reaction is not terminated at the right time, it is even possible for the entire contents of the reactor to solidify.

Moreover, it is not technically straightforward to introduce the amount of energy required for the cyclizing depolymerization into a stirred reactor and at the same time, offer the target product and the glycol which has formed and any which has been additionally introduced and unavoidably distills off with the target product, as large an evaporation surface as possible.

According to European Patent Application 929 07 653.7, this problem is solved by using a special, horizontal thin-film evaporator, although this must be operated at very high temperatures of >300° C. and with virtually neat (pure) polymeric feed, and problems arising from the formation of highly polymeric products can be particularly serious.

The above problems are overcome by the novel process in a simple and advantageous manner which is easy to carry out industrially. The invention provides a process for the preparation of macrocyclic esters, preferably esters comprising from 12 to 20 ring members, of the general formula (I):

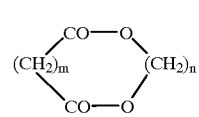
(I)

in which m is an integer from 6 to 14 and n is an integer from 2 to 12, which comprises heating (a) dicarboxylic acid glycol esters of the general formulae:

formula (I): I HO—$(CH_2)_n$—O—CO—$(CH_2)_m$—CO—O—$(CH_2)_n$—OH;

formula (III): H{O—$(CH_2)_n$—O—CO—$(CH_2)_m$—CO}$_x$—O—$(CH_2)$n—OH;

formula (IV): H{O—$(CH_2)_n$—O—CO—$(CH_2)_m$—CO—}$_x$—OH; and/or formula (V): HO—CO—$(CH_2)_m$—CO—{—O—$(CH_2)_n$—O—CO—$(CH_2)_m$—CO—}$_x$—OH, in which m and n are as defined above and x is an integer >1, preferably from 2 to 10;

(b) a glycol of the general formula:

formula (VI) HO—$(CH_2)_n$—OH, in which n has the same numerical value as in formulae (I) to (V), in an amount of from 1 to 50 times, preferably from 2 to 20 times, the molar amount, based on the ester V and the dicarboxylic acid units of esters (II) to (IV), and (c) an inert high-boiling reaction medium in an amount of from 0.1 to 20 times, preferably from 1 to 15 times and, in particular, from 2 to 10 times, the amount by weight, based on the total weight of esters (II) to (V), in the presence of (d) a catalyst; where the heating temperature is from 150 to 350° C., preferably from 180 to 300° C. and, in particular, from 200 to 280° C., at a reduced pressure of from about 0.1 to about 500 mbar, and preferably from 0.5 to 100 mbar, in an evaporator having a large surface area, as a result of which the macrocyclic ester (I) is produced with the elimination of glycol and is distilled off together with glycol (VI) and isolated by condensation.

Surprisingly, the novel process produces yields of macrocyclic esters (I) of >90% of theory, despite the presence of excess glycol which is expected to shift the transesterification equilibrium in the direction of the monomeric dicarboxylic acid bis(glycol) esters (V), i.e. expected to suppress the cyclization reaction.

DESCRIPTION OF THE PREFERRED EMBODIMENTS

The novel process is advantageously carried out continuously with recycling of the inert high-boiling medium, which contains the catalyst and unreacted esters (II) to (V). Preferably, the continuous process is carried out in such a way that the solution of the dicarboxylic acid glycol esters (II) to (V) in the corresponding glycol, which solution contains the catalyst, is introduced into the recycled inert high-boiling medium, and the resulting mixture is introduced into the evaporation zone, which is also the reaction zone, and the macrocyclic ester (I) and glycol (VI) formed are removed from this mixture by distillation. The starting materials, i.e. the esters (II) to (V), are largely reacted in only one pass. Thus, in an optimum procedure, only 1 to 10% of starting material, based on the inert high-boiling medium, remain unevaporated and, following enrichment with fresh starting material and glycol, are recycled to the evaporation zone. The residence time in the evaporator having a large surface area is advantageously from 0.5 to 10 minutes per pass. It is controlled by the performance of the pump which generates the cycle. After the steady state has been achieved, up to 100% of the starting materials are converted into the target product I. Over the course of an extended production process, which involves an initiation phase and a steady state, well over 95% of the starting materials, depending on the length of the process, are thus converted into the target product (I).

The esters (II) to (V) are derived from dicarboxylic acids and glycols (or dials). Suitable dicarboxylic acids have, for example, from 2 to 20, advantageously from 4 to 12, carbon atoms between the carboxyl groups. Examples include, but are not limited to succinic acid, adipic acid, suberic acid, sebacic acid (1,10-decanedioic acid), 1,12-dodecanedioic acid and brassylic acid (1,13-tridecanedioic acid). Of the suitable glycols (IV), which may contain, for example, from 2 to 12 carbon atoms between the hydroxyl groups, the following are not limiting examples: ethylene glycol, ethylene diglycol, 1,3-propanediol, 1,4-butanediol, 1,6-hexanediol, 1,8-octanediol and 1,12-dodecanediol.

A glycolic solution of the esters (II) to (V) which is suitable for carrying out the novel process can be prepared, for example, using customary esterification or transesterification catalysts by direct esterification of the dicarboxylic acid with the glycol (VI), by transesterification of a dicarboxylic acid dialkyl ester of an aliphatic, low molecular weight alcohol having, advantageously, from 1 to 6 carbon atoms, with the glycol (VI) with elimination of the aliphatic low molecular weight alcohol, or by depolymerization of a highly polymeric ester of the formulae (III) to (V), in which x is, for example, >10, with excess glycol (VI). In the latter case, highly polymeric esters (III) to (V) are thus degraded to give a mixture of monomeric esters (II) and relatively high molecular weight esters (III) having a lower value of x, advantageously from 2 to 10 (the formation of relatively high molecular weight esters (IV) and (V), which contain free carboxyl groups, is not favored as a result of the glycol excess). In all three cases mentioned, the formation of the monomeric dicarboxylic acid bis(glycol) ester (II) is preferred in the presence of an increasing excess of glycol (VI). If the amount of glycol (VI) is limited, e.g. to at most 20 mol of glycol per mol of dicarboxylic acid or dicarboxylic acid unit, starting materials (II) to (V) are obtained which contain relatively small amounts of monomeric ester (II) and large amounts of higher dicarboxylic acid ester (III). Solutions which contain virtually no monomeric esters (II) can only be prepared with very slight excesses of glycol (VI). In practice, esters (II) to (V) will always be present alongside one another. For example, solutions of the esters (II) to (V) in which the esters (III) to (V) are present in amounts of from 70 to 95% by weight, based on the total amounts of esters (II) to (V), can be used successively. Since all of the methods of preparation described give a mixture of molecules having a varying degree of oligomerization, x is always a mean value for the solution.

If the glycolic solutions of esters (II) to (V) are prepared in the manner described, they usually contain the required amounts of glycol (VI). If this is not the case or if an amount which is sufficient per se is to be increased for purposes of optimization, further glycol is added. Optimization can be achieved, for example, if, during the preparation of the glycolic solution of the esters (II) to (V), in the interest of a high space-time yield, less glycol (VI) has been added than is desirable for the cyclization reaction. Preferably, the glycol is present in an amount of from 2 to 20 times the molar amount, based on the dicarboxylic acid units of the esters (II) to (V).

Possible catalysts which may be used both for the preparation of the glycolic solutions of the esters (II) to (V) and also for the novel cyclization reaction are the customary acidic or basic esterification catalysts, which, as is known, are also transesterification catalysts. Examples of suitable catalysts are acids which are sufficiently stable under the process conditions, such as sulfuric acid, sodium hydrogen sulfate, phosphoric acid and sulfonic acids; also alkali metals and alkali metal alkoxides; compounds of magnesium, manganese, cadmium, iron, cobalt, tin, lead, aluminum and titanium. Preference is given to homogeneously dissolved catalysts of the Lewis acid type. The iron (III) complexes described in German Patent Application 198 08 845.0, which is also pending, can also be used advantageously as catalysts for the present invention.

The catalysts used for the preparation of the glycolic solutions of the starting materials (II) to (V) can generally simply remain in the solution, since they are, as stated, also catalysts which can be used for the novel cyclization reaction. This applies in particular when the catalysts are dissolved homogeneously. However, in addition or instead of the remaining catalyst used for the preparation of the glycolic solutions, catalyst may be introduced with the inert high-boiling reaction medium. If the process of the invention is carried out continuously, further catalyst can be added to the recycled inert high-boiling medium, which already contains catalyst.

It has proven to be advantageous if, in the evaporation zone, from 0.01 to 10% by weight of catalyst are present per mol of monomeric dicarboxylic acid bis(glycol) esters (II) or dicarboxylic acid units in the esters (III) to (V). If the process is carried out continuously, the desired catalyst concentration in the evaporation zone can be controlled by the circulation rate of the inert high boiling medium. At a high circulation rate, it is possible to provide high concentrations of catalyst in the evaporation zone. This is one advantage of the continuous variant of the novel process.

Examples of suitable inert high-boiling media, i.e. those boiling above >400° C. at atmospheric pressure, are higher glycol dialkyl ethers and polyalkylene glycol dialkyl ethers. The following specific examples may be mentioned: polyethylene glycol (1000) dimethyl ether (PEG DME 1000), PEG DME 2000, PEG DME 5000, polyethylene glycol (1000) diethyl ether (PEG DEE 1000), PEG DEE 2000, PEG DEE 5000 and dihexyl or didodecyl ethers of 1,12-dodecanediol or 1,16-hexadecanediol. The numbers refer to the molecular weights.

In addition to the presence of specific molar amounts of glycol, based on the ester (II) and the dicarboxylic acid units in the esters (III) to (V), the amount by weight of inert high-boiling medium, based on the total amounts by weight of the esters (II) to (V), is also an essential feature of the invention. The result of these measures is that extensive conversion of the esters (II) to (V) to the macrocyclic esters (I) is achieved in just one pass, so that in the case of continuous implementation of the process there is virtually no accumulation of nonvolatile highly polymeric esters (III) to (V) (where x=>10) in the recycled reaction medium. The required amount of inert, high-boiling medium is determined not only by the amount of esters (II) to (V) and glycol (VI) added per unit of time, but also by the optimum residence time in the evaporation zone, which depends inter alia on the equipment, in particular the type of evaporator and the recirculating performance of the pump, and also on the temperature in the evaporation zone. In each case, the relevant parameters must be matched to one another in such a way that from 0.1 to 20 times, advantageously from 2 to about 10 times, the amount by weight, based on the total amounts by weight of the esters (II) to (V), of inert high-boiling medium is present in the evaporation zone. A greater degree of dilution, i.e. a 20-fold or greater amount of inert high-boiling medium, offers no economic advantage, but neither is it a disadvantage for the progress of the reaction.

Suitable evaporators, which are also reactors, are any conventional evaporators having a large surface area, such as thin-film, falling-film, trickle film and short-path evaporators. In these cases, the required amount of heat can advantageously be introduced directly via the evaporator. If a recycle stream of the inert high-boiling medium is passed over a heat exchanger, then the reaction can also be carried out in a trickle bed reactor. Another suitable variant is a stirred reactor having a fixed-bed catalyst, which is connected to a customary evaporator having a large surface area via a circuit. Finally, it is possible to spray the preheated high-boiling reaction medium comprising starting material (II) to (V) and glycol (VI), in the presence of a catalyst, into an evaporator in which a heated inert carrier gas flows and carries out the macrocyclic ester (I) and excess glycol (VI), while the high-boiling reaction medium flows from the evaporator as a liquid. In suitable evaporators, the high-boiling reaction medium, which contains starting material (II) to (V), glycol (VI), catalyst and, after the reaction has progressed, also macrocyclic ester (I), is present in a thin film less than 2 cm in thickness, advantageously less than 0.5 cm in thickness, or in drop form, and thus offers a large, evaporation promoting specific surface area. The residence times of the high-boiling reaction medium during which the conversion from the starting material to the product is completed are relatively short, preferably 10 to 120 seconds. Large-surface area evaporators thus permit, at reaction temperatures suitable for the respective macrocyclic ester, an at least 80%, advantageously at least 90%, conversion of the starting material within a residence time of less than 5 minutes, advantageously of less than 2 minutes. In most cases the residence times are in the seconds range. In all cases, the distillate separates into two phases, the macrocyclic ester (I) being the upper phase and the glycol (VI) being the lower phase.

It is surprising that the novel reaction proceeds so well especially in an evaporator having a large surface area because under these conditions, the glycol, whose presence in a molar excess is an important feature of the process of the invention, is the substance with the lowest boiling point of all the components present in the reaction mixture and is removed particularly quickly from the reaction mixture.

Surprisingly, the novel process for the preparation of macrocyclic esters also leads to high, almost quantitative yields even when, in addition to the monomeric ester (II) and higher molecular weight esters (III) to (V) (x=2 to 10), highly polymeric esters (III) to (V) (x=>10) are present in considerable amounts. Should, however, after a prolonged period, undesirably large amounts of highly polymeric esters (III) to (V) accumulate in the recycled inert high-boiling medium, it is also possible to depolymerize these and convert them into macrocyclic ester (I) by temporarily increasing the amount of glycol added. Alternatively, it is also possible to use concomitantly some of the inert high-boiling medium enriched with highly polymeric esters in the described preparation of the glycolic solution of the esters (II) to (V). Degradation to higher molecular weight (x=2 to 10) esters (III) to (V) and monomeric ester (II) also takes place in this instance.

Having generally described this invention, a further understanding can be obtained by reference to certain specific examples which are provided herein for purposes of illustration only and are not intended to be limiting unless otherwise specified.

EXAMPLES

The following Examples are also recited in the priority document, German patent application 198 088 43.4, filed Mar. 3, 1998, which is incorporated herein by reference in its entirety.

Example 1

X kg of oligomeric dicarboxylic acid bisglycol ester of the formula (II) where m=11 and n=2, which contains 0.1% by weight of the monosodium salt of the iron (III) ethylenediaminetetraacetic acid complex, and Y kg of ethylene glycol are fed by means of metering pumps to a reactor which contains Z kg of polyethylene glycol (2000) dimethyl ether as high-boiling medium for cyclizing depolymerization. The reactor consists of a heated falling-film evaporator having a surface area of about 1.5 $m^2$ and a still (distillation apparatus) incorporated into the heating cycle and having a volume of about 50 l and a return line to the top of the falling-film evaporator, which is equipped with a prewarmer on the starting material side.

The vapors are passed through a vapor pipe and a condenser. A separation vessel is connected downstream of the distillation receiver. The materials drawn off from this separation vessel as the upper phase is ethylene brassylate containing about 5% by weight of ethylene glycol. Distillation without appreciable separation efficiency produces pure ethylene brassylate. The lower separated phase is ethylene glycol containing from 2 to 3% by weight of ethylene brassylate, which can be used together with fresh ethylene glycol for a fresh batch.

The feed amounts, process conditions and results for a number of batches are given in Table 1 below.

Example 2

X kg of oligomeric dicarboxylic acid bisglycol ester of the formula (II) where m=11 and n=2, which contains 0.1% by weight of iron (III) complex catalyst (iron(III) acetylacetonate), and Y kg of ethylene glycol are fed by means of metering pumps to a reactor which contains Z kg of polyethylene glycol (2000) dimethyl ether as high-boiling medium for cyclizing depolymerization. To improve the reaction rate, about 0.1% by weight of the catalyst is added to the high-boiling medium. The reactor consists of a 250-l stirred reactor to which is attached a heated falling-film evaporator having a surface area of about 1.0 $m^2$. The bottom product from the reactor is recycled to the falling film evaporator using a circulating pump, which increases the evaporation efficiency compared with simple distillation from the reactor.

The vapors are passed through a vapor pipe and a condenser. A separation vessel is connected downstream of the distillation receiver. The material drawn off as the upper phase from this separation vessel is ethylene brassylate containing about 5% by weight of ethylene glycol. Distillation without appreciable separation efficiency produces pure ethylene brassylate. The lower separated phase is ethylene glycol containing from 2 to 3% by weight of ethylene brassylate, which can be used together with fresh ethylene glycol for a fresh batch. The feed amounts, process conditions and results for a number of batches are given in Table 2 below.

TABLE 1

| Batch | High-Boiling medium Z (kg) | p min (mbar) | T max (° C.) | Average residence time in the reactor (sec) | Amount of Y | Amount of X | Yield of pure ethylene brassylate (kg) | Yield of pure ethylene brassylate (%) |
|---|---|---|---|---|---|---|---|---|
| 1.1 | 15 | 20 | 270 | 180 | 30 | 10 | 9.5 | 95 |
| 1.2 | 15 | 20 | 270 | 180 | 27 | 13 | 12.1 | 93 |
| 1.3 | 15 | 30 | 280 | 360 | 38 | 12 | 11.5 | 96 |
| 1.4 | 35 | 30 | 280 | 360 | 42 | 11 | 10.6 | 96 |
| 1.5 | 35 | 5 | 260 | 30 | 44 | 14 | 12.9 | 92 |
| 1.6 | 35 | 5 | 260 | 30 | 64 | 16 | 14.9 | 93 | p min: minimum pressure
T max: maximum temperature

TABLE 2

| Batch | High-Boiling medium Z (kg) | p min (mbar) | T max (° C.) | Average residence time in the reactor (sec) | Amount of Y | Amount of X | Yield of pure ethylene brassylate (kg) | Yield of pure ethylene brassylate (%) |
|---|---|---|---|---|---|---|---|---|
| 2.1 | 105 | 20 | 270 | 160 | 35 | 11 | 10.0 | 91 |
| 2.2 | 125 | 20 | 270 | 540 | 29 | 10 | 9.2 | 92 |
| 2.3 | 125 | 30 | 280 | 1,080 | 48 | 12 | 11.5 | 96 |
| 2.4 | 145 | 30 | 280 | 1,080 | 50 | 11.5 | 11.2 | 97 |
| 2.5 | 145 | 5 | 270 | 90 | 46 | 11 | 10.5 | 99 |
| 2.6 | 155 | 5 | 260 | 90 | 67 | 16.5 | 5.5 | 94 | p min: minimum pressure
T max: maximum temperature

Example 3

X kg of oligomeric dicarboxylic acid bisglycol ester of the formula (II) where m=11 and n=2, which contains 0.1% by weight of iron(III) complex catalyst ($K_3\{Fe(CN)_6\}$), and Y kg of ethylene glycol are fed by means of metering pumps to a reactor which contains Z kg of polyethylene glycol (2000) dimethyl ether as high-boiling medium for cyclizing polymerization. The reactor consists of a heated falling-film evaporator having a surface area of about 1.5 m² and a still incorporated into the heating cycle and having a volume of about 50 l and a return line to the top of the falling-film evaporator, which is equipped with a pre-warmer on the starting material side.

The vapors are passed through a vapor pipe and a condenser. A separation vessel is connected downstream of the distillation receiver. The material drawn off as the upper phase from this separation vessel is ethylene glycol dodecanedioate containing about 4% by weight of ethylene glycol. Distillation without appreciable separation efficiency produces pure ethylene glycol dodecanedioate. The lower separated phase is ethylene glycol containing from 2 to 3% by weight of ethylene glycol dodecanedioate, which can be used together with fresh ethylene glycol for a fresh batch.

The feed amounts, process conditions and results for a number of batches are given in Table 3 below.

by means of metering pumps to a reactor which contains Z kg of polyethylene glycol (2000) dimethyl ether as high-boiling medium for cyclizing polymerization. The reactor consists of a heated falling-film evaporator having a surface area of about 1.5 m² and a still incorporated into the heating cycle and having a volume of about 50 l. In contrast to Examples 1 and 3, the still discharge was not recycled to the top of the falling-film evaporator.

The vapors are passed through a vapor pipe and a condenser. A separation vessel is connected downstream of the distillation receiver. The material drawn off as the upper phase from this separation vessel is ethylene glycol dodecanedioate containing about 4% by weight of ethylene glycol. Distillation without appreciable separation efficiency produces pure ethylene glycol dodecanedioate. The lower separated phase is ethylene glycol containing from 2 to 3% by weight of ethylene glycol dodecanedioate, which can be used together with fresh ethylene glycol for a fresh batch.

The feed amounts, process conditions and results for a number of batches are given in Table 4 below.

TABLE 3

| Batch | High-Boiling medium Z (kg) | p min (mbar) | T max (° C.) | Average residence time in the reactor (sec) | Amount of Y | Amount of X | Yield of pure ethylene brassylate (kg) | (%) |
|---|---|---|---|---|---|---|---|---|
| 3.1 | 25 | 20 | 270 | 190 | 35 | 11 | 12.0 | 94 |
| 3.2 | 25 | 20 | 275 | 120 | 27 | 6.5 | 6.0 | 92 |
| 3.3 | 15 | 30 | 280 | 330 | 18 | 4.5 | 4.2 | 93 |
| 3.4 | 35 | 30 | 280 | 300 | 42 | 10.5 | 10.2 | 97 |
| 3.5 | 35 | 15 | 260 | 40 | 64 | 12 | 10.5 | 89 |
| 3.6 | 35 | 15 | 270 | 50 | 70 | 19 | 17.0 | 90 | p min: minimum pressure
T max: maximum temperature

Example 4

X kg of oligomeric dicarboxylic acid bisglycol ester of the formula (II) where m=11 and n=2, which contains 0.1% by

TABLE 4

| Batch | High-Boiling medium Z (kg) | p min (mbar) | T max (° C.) | Average residence time in the reactor (sec) | Amount of Y | Amount of X | Yield of pure ethylene brassylate (kg) | (%) |
|---|---|---|---|---|---|---|---|---|
| 4.1 | 25 | 20 | 270 | 190 | 35 | 11 | 5.0 | 46 |
| 4.2 | 25 | 20 | 275 | 120 | 27 | 6.5 | 2.5 | 39 |
| 4.3 | 15 | 30 | 280 | 330 | 18 | 4.5 | 2.9 | 64 |
| 4.4 | 35 | 30 | 280 | 300 | 42 | 10.5 | 6.4 | 61 |
| 4.5 | 35 | 15 | 260 | 40 | 64 | 12 | 375 | 31 |
| 4.6 | 35 | 15 | 270 | 50 | 70 | 19 | 5.3 | 28 | p min: minimum pressure
T max: maximum temperature weight of monopotassium salt of iron(III) ethylenediaminetetraacetic acid complex, and Y kg of ethylene glycol are fed As in the preceding examples, the yield refers here to weight ester used, and thus disregards the unreacted component thereof which remains in the still discharge. The example shows the advantageous effect of the circuit which was used in Examples 1 to 3 and leads to reaction of these components too.

What is claimed is:

1. A process for the preparation of a macrocyclic ester of formula (I):

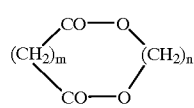

(I)

comprising,
heating the following components:
component (a) comprising dicarboxylic acid (bis) glycol esters of the formulae:
formula (II) HO—$(CH_2)_n$—O—CO—$(CH_2)_m$—CO—O—$(CH_2)_n$—OH;
formula (III) H$\{$O—$(CH_2)_n$—O—CO—$(CH_2)_m$—CO$\}_x$—O—$(CH_2)_n$—OH;
formula (IV) H$\{$O—$(CH_2)_n$——O—CO—$(CH_2)_m$—CO—$\}_x$—OH and
formula (V) HO—CO—$(CH_2)_m$—CO—$\{$—O—$(CH_2)_n$—O—CO—$(CH_2)_m$—CO—$\}_x$—OH;
component (b) a glycol of formula (VI) HO—$(CH_2)_n$—OH in an amount of from 1 to 50 times the molar amount, based on ester of formula (V) and the dicarboxylic acid units of esters of formulae (III) to (IV); in the presence of
component (c) an inert high-boiling reaction medium in an amount of from 0.1 to 20 times the amount by weight, based on the total weight of esters of formulae (II) to (V); and
component (d) a catalyst; at a temperatures of from 150 to 350° C. and at a reduced pressure of from about 0.1 to about 500 mbar, in an evaporator having a large surface area, thus producing said macrocyclic ester (I) by elimination of glycol of formula (VI);
distilling off said macrocyclic ester (I) and glycol (VI); and
isolating said macrocyclic ester (I) by condensation;
where m is an integer from 6 to 14, n is an integer from 2 to 12, and x is an integer >1; and wherein said high-boiling reaction medium has a boiling point above 400° C.

2. The process as claimed in claim 1, wherein said process is carried out continuously comprising recycling the inert high-boiling medium comprising the catalyst and unreacted esters of formulae (II) to (V), and adding additional esters of formulae (II) to (V) and additional glycol (VI) to the recycle mixture.

3. The process as claimed in claim 1, wherein the glycol is present in an amount of from 2 to 20 times the molar amount, based on the dicarboxylic acid units in esters (II) to (V).

4. The process as claimed in claim 1, wherein the temperature is from 180 to 300° C.

5. The process as claimed in claim 1, wherein the temperature is from 200 to 280° C.

6. The process as claimed in claim 1, wherein the pressure is from 0.5 to 100 mbar.

7. The process as claimed in claim 1, wherein the inert high boiling medium (c) is one or more solvents selected from the group consisting of inert higher glycol dialkyl ethers and polyalkylene glycol dialkyl ethers.

8. The process as claimed in claim 1, wherein the inert high boiling medium (c) is present in an amount of from 1 to 15 times the amount by weight, based on the total amount by weight of esters (II) to (V).

9. The process as claimed in claim 1, wherein the inert high boiling medium (c) is present in an amount of from 2 to 10 times the amount by weight, based on the total amount by weight of esters (II) to (V).

10. The process as claimed in claim 1, wherein the esters (II) to (V) and the glycol (VI) are present in the form of a glycolic solution of an ester which has been produced by one of the following methods in the presence of a catalyst: esterifying a dicarboxylic acid with excess glycol, by transesterifying a dicarboxylic dialkyl ester having alkyl groups containing from 1 to 6 carbon atoms with excess glycol or by depolymerizing a polymeric ester (III) to (V) with excess glycol, wherein said x in said polymeric ester is >10; wherein said catalyst is the same or different than the catalyst component (a).

11. The process as claimed in claim 1, wherein the catalyst (d) is sulfuric acid, phosphoric acid or a sulfonic acid.

12. The process as claimed in claim 1, wherein the catalyst (d) is an alkali metal or alkali metal alkoxide.

13. The process as claimed in claim 1, wherein the catalyst (d) is one or more compound selected from the group consisting of magnesium, manganese, cadmium, iron, cobalt, tin, lead, aluminum and titanium compound.

14. The process as claimed in claim 10, wherein said catalyst is the same catalyst as catalyst component (d).

15. The process as claimed in claim 2, further comprising adding catalyst (d) to the recycled inert high-boiling medium.

16. The process as claimed in claim 1, wherein the evaporator having a large surface area is a thin-film, falling-film or short-path evaporator.

17. The process as claimed in claim 1, wherein the evaporator having a large surface area is a trickle bed of a column.

18. The process as claimed in claim 1, wherein x in component (a) is 2 to 10.

19. The process as claimed in claim 1, wherein component (b) is present in an amount of from 2 to 20 times the molar amount, based on ester of formula (V) and the dicarboxylic acid units of esters of formulae (III) to (IV).

20. The process as claimed in claim 1, wherein component (c) is present in an amount of from 1 to 15 times the amount by weight, based on the total weight of esters of formulae (II) to (V).

* * * * *